(12) United States Patent
Whiteford

(10) Patent No.: US 7,192,420 B2
(45) Date of Patent: Mar. 20, 2007

(54) OSTOMY ADAPTER WITH MULTIPLE ADHESIVES FOR RELIABLE SEALING

(76) Inventor: Bruce W. Whiteford, 8024 Northern Dr., Crystal, MN (US) 55427

( * ) Notice: Subject to any disclaimer, the term of this patent is extended or adjusted under 35 U.S.C. 154(b) by 248 days.

(21) Appl. No.: 10/637,460

(22) Filed: Aug. 8, 2003

(65) Prior Publication Data

US 2005/0033249 A1    Feb. 10, 2005

(51) Int. Cl.
*A61F 5/443* (2006.01)
*A61F 5/445* (2006.01)

(52) U.S. Cl. .................. 604/336; 604/339; 604/332

(58) Field of Classification Search ............... 604/344, 604/377, 278, 332, 336, 339
See application file for complete search history.

(56) References Cited

U.S. PATENT DOCUMENTS

| | | | | |
|---|---|---|---|---|
| 3,330,271 | A | * | 7/1967 | Hozier .................. 128/205.29 |
| 4,775,374 | A | * | 10/1988 | Cilento et al. ............. 604/339 |
| 5,000,748 | A | | 3/1991 | Fenton |
| 5,004,464 | A | * | 4/1991 | Leise, Jr. .................. 604/338 |
| 5,147,340 | A | * | 9/1992 | Lavender .................. 604/344 |
| 5,160,330 | A | * | 11/1992 | Cross ........................ 604/339 |
| 5,364,379 | A | * | 11/1994 | Ozenne et al. ............. 604/342 |
| 5,545,154 | A | * | 8/1996 | Oberholtzer ................ 604/336 |
| 5,618,276 | A | * | 4/1997 | Leise et al. ................. 604/336 |
| 5,834,009 | A | | 11/1998 | Sawers et al. |
| 5,865,819 | A | * | 2/1999 | Cisko et al. ................ 604/339 |
| 5,947,942 | A | * | 9/1999 | Galjour ...................... 604/345 |
| 6,095,996 | A | | 8/2000 | Steer et al. |
| 6,332,879 | B1 | | 12/2001 | Nielsen et al. |
| 6,387,082 | B1 | | 5/2002 | Freeman |
| 6,520,943 | B1 | | 2/2003 | Wagner |
| 6,790,200 | B2 | * | 9/2004 | Fenton ....................... 604/338 |
| 2004/0059306 | A1 | * | 3/2004 | Tsal et al. ................... 604/332 |

FOREIGN PATENT DOCUMENTS

| | | | |
|---|---|---|---|
| EP | 0081907 A1 | * | 6/1983 |
| GB | 2041753 A | * | 9/1980 |

OTHER PUBLICATIONS

Advertisement from *OQ Ostomy Quarterly*, Summer 2003, vol. 40, No. 4, p. 9, on a VPI Non-Adhesive Urosomy System offered by Cook Would/Ostomy/Continence of Spencer, Indiana.
Advertisement from *OQ Ostomy Quarterly*, Summer 2003, vol. 40, No. 4, p. 15, on a Ultraseal Flexible Barrier Ring offered by Marlen Manufacturing & Development Company of Bedord, Ohio.

* cited by examiner

*Primary Examiner*—Tatyana Zalukaeva
*Assistant Examiner*—Laura C Hill
(74) *Attorney, Agent, or Firm*—Merchant & Gould PC

(57) ABSTRACT

An adapter arrangement for use with a waste collection construction, for example an ostomy appliance, includes a flange defining a stoma-receiving aperture and a tubular wall extending from the flange. The flange includes first and second opposite surfaces, each having an adhesive layer disposed thereon. The tubular wall has an inner, stoma-contacting surface and an opposite outer surface. The inner, stoma-contacting surface includes a stoma-contacting adhesive layer. A collection system includes an adapter arrangement, and a waste collection pouch. The waste collection pouch includes a pouch wall and a mouth. There is a lip on the pouch wall circumscribing the mouth, and an adhesive collar circumscribing the lip. The tubular wall of the adapter arrangement is received within the mouth, and the adhesive layer on the flange of the adapter arrangement secures the flange to the pouch lip.

20 Claims, 4 Drawing Sheets

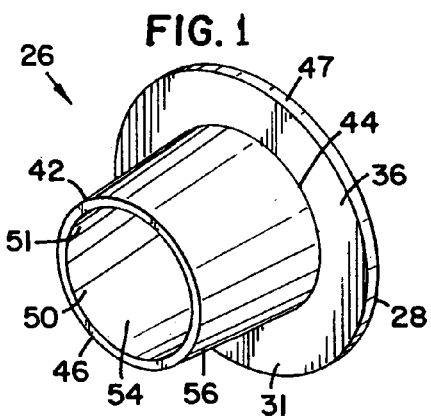
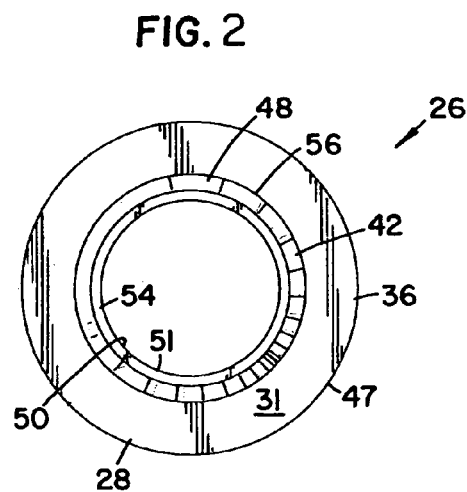
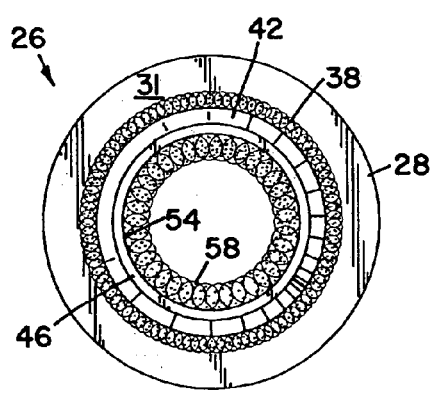
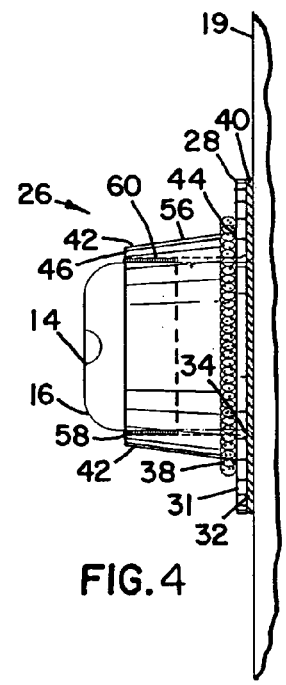

US 7,192,420 B2

OSTOMY ADAPTER WITH MULTIPLE ADHESIVES FOR RELIABLE SEALING

TECHNICAL FIELD

This disclosure is directed to the field of ostomy appliances.

BACKGROUND

Ostomy appliances generally include a bag or pouch for collecting bodily waste discharged from their surgically created stoma. The bag is connected to a pad or surgical dressing that is in contact with the patient's skin and surrounds the stoma. The pouch is used to collect the waste and then emptied as needed. A stoma is usually located on a patient's belly above the belt line, and can be about 0.5–2 inches in diameter and protrude about 0.5–1.5 inches, typically, about 7/8 of an inch. The pouch is placed over the stoma using a small bead of seal paste applied at the base of the stoma to make a watertight seal. This pouch seal typically lasts about 1–2 days, before the seal is broken due to, for example, bodily perspiration that causes the seal paste to release from the skin. This can result in the pouch falling off or leaking, which obviously, is undesirable.

Improvements in securing ostomy appliances to a stoma on a human body are desirable.

SUMMARY

In general, an adapter arrangement for use with a waste collection construction, for example an ostomy appliance, is provided. The adapter arrangement includes a flange defining a stoma-receiving aperture and a tubular wall extending from the flange. The flange includes first and second opposite surfaces, each having an adhesive layer disposed thereon. The tubular wall has an inner, stoma-contacting surface and an opposite outer surface. The inner, stoma-contacting surface includes a stoma-contacting adhesive layer.

In general, a human waste collection system for use with a stoma-containing body part projecting from a human body and surrounded by a portion of exterior skin is provided. The collection system includes an adapter arrangement, as characterized above, and a waste collection pouch. The waste collection pouch includes a pouch wall defining an interior waste collecting volume and a mouth providing access to the volume. There is a lip on the pouch wall circumscribing the mouth, and an adhesive collar circumscribing the lip. The tubular wall of the adapter arrangement is received within the mouth, and the adhesive layer on the flange of the adapter arrangement secures the flange to the pouch lip.

In general, a method is provided of collecting human waste from a human body having a stoma-containing body part projecting therefrom and surrounded by a portion of exterior skin. The method includes providing an adapter arrangement having a flange and an extending tubular wall, the flange and the tubular wall defining a stoma-receiving aperture. The adapter arrangement is oriented over the stoma-containing body part by placing the stoma-containing body part through the stoma-receiving aperture. The stoma-containing body part is adhered to the tubular wall with adhesive between an outer portion of the stoma-containing body part and an inner surface of the tubular wall. A waste collection pouch is provided having a mouth, a surrounding lip, and a pouch wall. The waste collection pouch is oriented over the adapter arrangement by inserting the tubular wall through the mouth. The waste collection pouch is adhered to the adapter arrangement with adhesive between the flange and the surrounding lip.

BRIEF DESCRIPTION OF THE DRAWINGS

FIG. 1 is a perspective view of one embodiment of an adapter arrangement constructed in accordance with principles of this disclosure;

FIG. 2 is a front elevational view of the adapter arrangement of FIG. 1;

FIG. 3 is a front elevational view, similar to the view in FIG. 2, and showing the application of adhesive or paste;

FIG. 4 is a side elevational view showing the adapter arrangement oriented over a stoma and with the existence of adhesive or paste;

DETAILED DESCRIPTION

Figure 5:
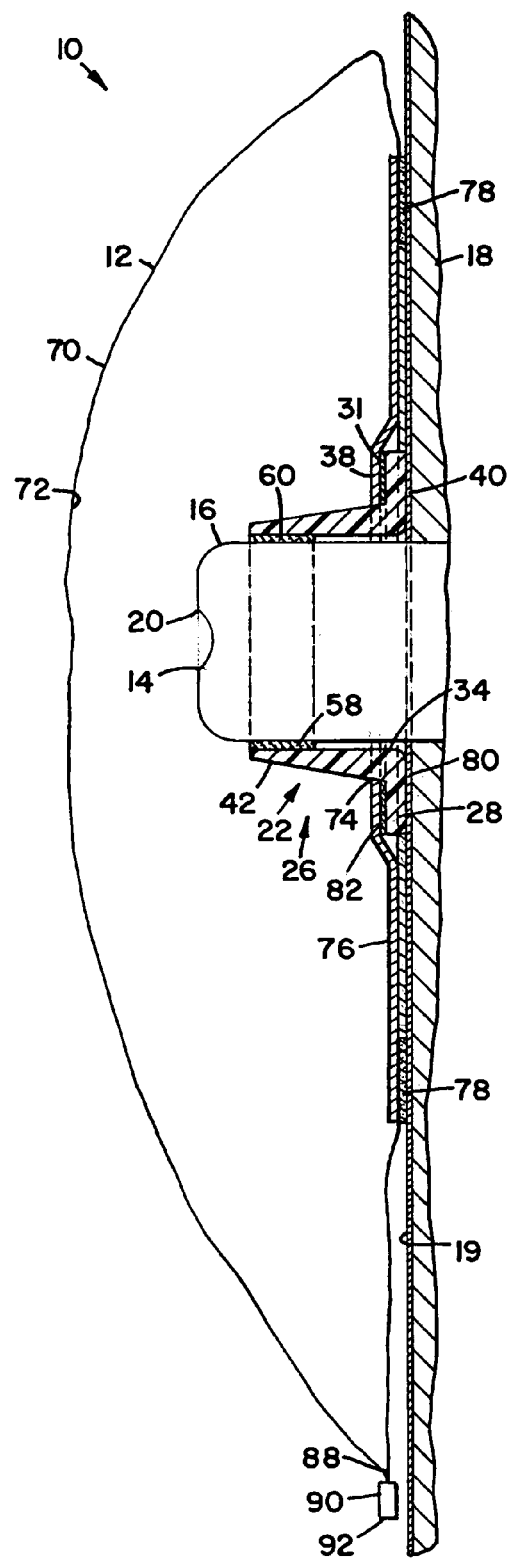
FIG. 5 is a schematic, partial cross-sectional view, with parts broken away, showing a waste collection system including the adapter arrangement oriented over a stoma and with a waste collection pouch oriented thereover.

Attention is first directed to FIG. 5. FIG. 5 illustrates a waste collection system at 10. In connection with surgery for a number of diseases in the gastro intestinal tract, a consequence is, in many cases, that the colon, the ileum, or the urethra has been exposed surgically, and the patient is left with an abdominal stoma. The effluents or waste products of the body, which are conveyed through these organs, are discharged through the stoma. The waste products are collected in a pouch, illustrated here at 12, in fluid connection with the stoma, illustrated here at 14. Also, in connection with a fistula, the person will have to rely on the pouch 12 to collect bodily material emerging from the stoma 14. In FIG. 5, a body part 16, which could be the colon, the ileum, or the urethra, is shown schematically emerging from a human body 18. The body part 16 has an aperture or hole 20, commonly called the stoma 14. In use, material from the body part 16 flows through the stoma 14 and into the pouch 12. As used herein, the term "stoma" generally refers to the hole 20 and the body part 16 defining the hole 20. The body part 16 will often be referred to herein as a "stoma-containing body part 16."

In accordance with principles of this disclosure, there is a mechanism, or guard, at 22 that isolates the stoma 14 from skin 19 on the body 18. The mechanism 22, among other things, helps to reduce irritation to the skin 19 by creating a reliable seal between mechanism 22 and stoma 14. The mechanism 22 also provides protection for the stoma 14 if the pouch 12 or the stoma 14 is disturbed or bumped.

In accordance with principles of this disclosure, the mechanism 22 is embodied herein as an adapter arrangement 26. Attention is directed to FIGS. 1–4, in which adapter arrangement 26 is illustrated. In the illustrated embodiment, the adapter arrangement 26 includes a flange 28 having first and second opposite surfaces 31, 32 and defining a stoma-receiving aperture 34. As illustrated herein, the flange 28 is embodied as a generally flat member 36 having the stoma-receiving aperture 34 therewithin. In the particular one shown, the flange 28 is generally circular. Of course, in other embodiments, the flange 28 need not be circular and can be a variety of other geometrical shapes.

The flange 28, in the preferred embodiment, is capable of and is typically used to hold adhesive or paste. FIG. 3 shows a first flange adhesive layer 38 deposited on the first surface 31. In FIG. 3, the adhesive layer 38 is shown as covering only a partial amount of the first surface 31. In other embodiments, the first flange adhesive layer 38 can cover most of or the entire amount of the first surface 31. FIG. 4 shows a second flange adhesive layer 40 deposited on the second surface 32 of the flange 28. In FIG. 4, the second flange adhesive layer 40 is shown in use as being attached to the skin 19. The first flange adhesive layer 38 is useable to secure the adapter arrangement 26 to a portion of the pouch 12. This is shown in FIG. 5 and described in further detail below with respect to FIG. 5.

Still in reference to FIGS. 1–4, the adapter arrangement 26 further includes a tubular wall 42 extending from the first surface 31 of the flange 28. The tubular wall 42 includes a base end 44 that is immediately adjacent to the first surface 31 of the flange 28, and a free end 46 projecting or extending from the flange 28. As such, the wall 42 is cantilevered from the flange 28. The wall 42 is tubular in that it forms a surrounding, closed wall 48 and defines an open passage 50 therein. The open passage 50 is also a wall stoma-receiving aperture 51 because of its preferred use in connection with the stoma-containing body part 16.

The tubular wall 42 includes an inner, stoma-contacting surface 54 and an opposite, outer surface 56. In the preferred embodiment illustrated, the inner stoma-contacting surface 54 includes a stoma-contacting adhesive layer 58. This adhesive layer 58 is shown schematically in FIG. 3. The adhesive layer 58 is shown, in its preferred use, in FIG. 4 as forming a seal 60 between the stoma-containing body part 16 and the wall 42 of the adapter arrangement 26.

From a review of FIGS. 1–4, it can be appreciated that the flange stoma-receiving aperture 34 and the wall stoma-receiving aperture 51 are coaxial and are in fluid communication with each other. As such, material that flows through the flange stoma-receiving aperture 34 also flows through the wall stoma-receiving aperture 51.

In preferred embodiments, the length of the wall 42 will be sufficient to hold a sufficient amount of adhesive or paste at layer 58 in order to form a good reliable seal 60 between the stoma-containing body part 16 and the wall 42. This seal 60 inhibits material that is expelled through the stoma 14 into the pouch 12 from passing between the body part 16 and the wall 42 of the adapter arrangement 26. This helps to prevent the materials in the pouch 12 from leaking from the pouch 12 and irritating the skin 19. Because the wall 42, in preferred embodiments, has a surface area that is large enough to create a good reliable seal 60, in certain preferred implementations, the wall 42 has a length that is at least 0.5 inch. In certain preferred arrangements, the wall 42 will have a length that is twice that of a rim width of the flange 28. By the term "rim width", it is meant the length between the base end 44 and the outer periphery 47 of the flange 28, drawn as the shortest straight line between those points.

As can be seen in FIG. 4, the tubular wall 42 extends from the flange 28 at an angle. That is, in the particular embodiment shown, the outer surface 56 does not extend from the flange 28 as a perfect right angle, but instead slants inwardly from an otherwise perpendicular surface. This degree of slant is referred to herein as an angle of declination. The angle of declination can be between 2° and 15°. In one particular embodiment, the angle of declination is about 8°.

In reference now to FIG. 5, the adapter arrangement 26 is shown in use as part of the waste collection system 10. The pouch 12 illustrated can be a variety of pouches or ostomy appliances. In the one shown, the pouch 12 includes a pouch wall 70 defining an interior waste collecting volume 72 and an open mouth 74 providing access to the open volume 72. In the particular one shown, there is also a lip 76 circumscribing the mouth 74. Further, there is an adhesive collar 78 circumscribing the lip 76. In the embodiment shown, the adhesive collar 78 is used to secure the pouch 12 to the skin 19.

In FIG. 5, the pouch 12 is shown to have an opening 88 that is closed by a closure 90. The closure 90 can be a pressure clip, or alternatively, a zipper closure 92. In that way, the pouch 12 can be conveniently opened and closed to permit the emptying of the pouch 12 or the release of gases therewithin. By "zipper closure" it is meant a structure having opposite interlocking or mating profiled elements that, under pressure, will interlock and close the region between the profiles.

The example pouch 12 illustrated in FIG. 5 is used with the adapter arrangement by passing the adapter tubular wall 42 through the mouth 74, such that the lip 76 circumscribes the wall 42. In the one shown, the lip 76 is secured to the adapter arrangement 26 by the first flange adhesive layer 38 being between and against the lip 76 and the first surface 31 of the flange 28.

As can be seen in FIG. 5, the stoma-contacting adhesive layer 58 removably secures the adapter arrangement 26 to the body part 16 having the stoma 14. As can also be appreciated, the second flange adhesive layer 40 removably secures the adapter arrangement 26 to a portion of exterior skin to form seal 80. Seal 80 helps to secure the adapter arrangement 26 to the human. The interface between the first flange adhesive layer 38 and the lip 76 forms a seal 82 between and against the flange 28 of the adapter arrangement 26 and the lip 76 of the pouch 12. Should seal 60 fail for some reason and permit material in the pouch interior 72 to pass between the body part 16 and the inner stoma-contacting surface 54, the seal 80 will stop the material from further spreading and irritation of the skin 19. The seal 82 between the lip 76 and the first surface 31 of the flange 28 helps to prevent passage of material from the interior volume 72 of the pouch 12 and onto the skin 19. The seal 82 helps to contain the material in the pouch interior 72.

A method of collecting human waste from a human body having a stoma-containing body part is provided. For example, the stoma-containing body part is shown at 16 having the stoma 14. The method includes providing an adapter arrangement, such as adapter arrangement 26 having flange 28 and an extending tubular wall 42. The flange 28 and the tubular wall 42 define stoma-receiving aperture 51. The adapter arrangement 26 is oriented over the stoma-containing body part 16 by placing the stoma-containing body part 16 through the stoma-receiving aperture 51. Next, the stoma-containing body part 16 is adhered to the tubular wall 42 with a paste or adhesive 58 between an outer portion of the stoma-containing body part 16 and the inner surface 54 of the tubular wall 42. The waste collection pouch 12 is provided having mouth 74, surrounding lip 76, and pouch wall 70. The waste collection pouch is oriented over the adapter arrangement 26 by inserting the tubular wall 42 through the mouth 74. The pouch 12 is adhered to the adapter arrangement 26 with adhesive between the flange 28 and the surrounding lip 76.

In preferred implementations, the adapter arrangement 26 is secured to the exterior skin 19 by adhering the flange 28 to the exterior skin along a side 32 of the flange 28 that is opposite of contact with the surrounding lip 76 of the pouch 12.

In preferred implementations, the waste collection pouch 12 is further secured to the exterior of the skin 19. This can be done, for example, with adhesive collar 78.

In some embodiments, the adapter arrangement 26 is constructed of a soft, rubber or rubber-like material that will withstand waste from the body. The adapter arrangement 26 is sized to fit the body part 16 defining the stoma 14. In some examples, the aperture 34 defined by the flange 28 is circular and has an inner diameter of between 0.5 and 2.5 inches.

In some embodiments, the lip 76 on the pouch 12 is rubber. Because the adapter arrangement 26 provides good, effective seals at 60, 80, and 82, the lip 76 can be made of a soft cloth. When made as a soft cloth, the lip 76 can have a therapeutic effect and aid in healing irritated skin in the vicinity of the stoma 14. The lip 76, when in soft cloth form or in its rubber form, can be coated with medications for promoting healing or other therapeutic effects. The lip 76 can also be made of the same material as the pouch wall 70, and in some cases, be thicker than the pouch wall 70.

The adhesives used herein are conventional, off-the-shelf, medical pastes, such as the type of paste provided by Hollister.

Figure 6:
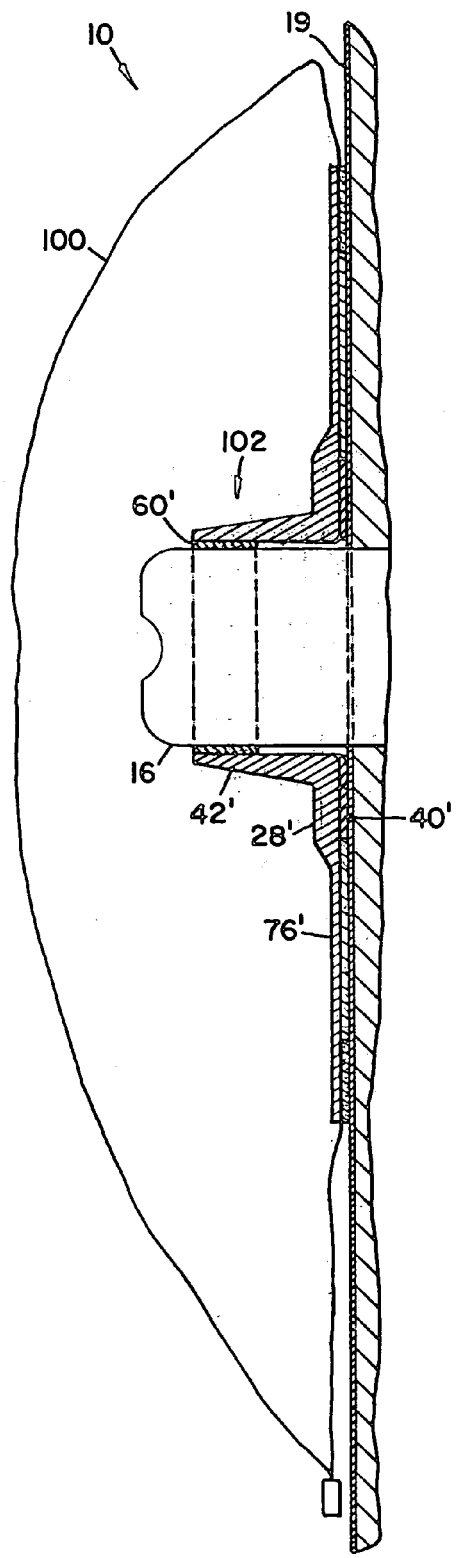
FIG. 6 is a schematic, partial cross-sectional view, analogous to FIG. 5, and depicting another embodiment of a waste collection system.

FIG. 6 shows an alternate embodiment of a waste collection system 10. In FIG. 6, there is shown a pouch 100 that includes an adapter arrangement 102 that is an integral part of it. It can be seen how the tubular wall 42' is the same part of and merely an extension of the lip 76'. In this embodiment, the flange 28' is just part of and an extension of the lip 76'. Seals 60' and 40' are formed between the pouch 100 and: (i) the stoma-containing body part 16; and (ii) the skin 19, respectively.

Figure 7:
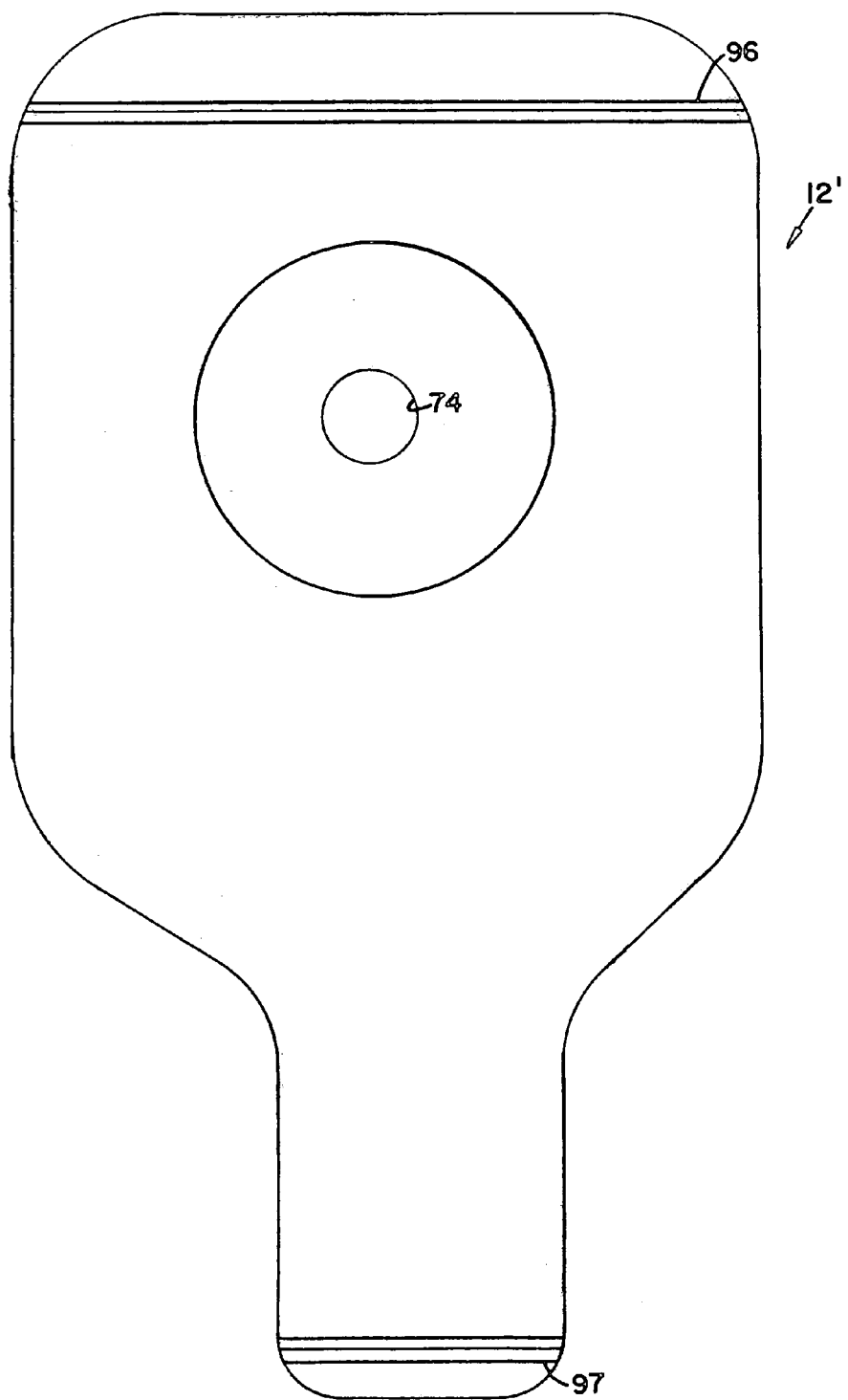
FIG. 7 is a schematic top plan view of a variation of a waste collection pouch useable with systems in accordance with principles of this disclosure.

In an alternate embodiment, FIG. 7, the pouch 12 is shown with a pair of open ends closeable at zipper closures 96, 97. This results in a flushable pouch 12'. The pouch 12' can be emptied by opening both zipper closures 96 and 97 and allowing gravity to drain the contents through the opening at zipper closure 97. A cleaning solution, such as soapy water, can then be placed through the opening at zipper closure 96 to clean the pouch interior and help flush the contents. In addition, either zipper closure 96 or 97 can be selectively opened to permit the convenient release of gases from within the pouch 12'.

I claim:

1. An adapter arrangement for use with a waste collection construction; the adapter arrangement comprising:
   (a) a flange having first and second opposite surfaces and defining a stoma-receiving aperture;
      (i) the first surface of the flange including a first flange adhesive layer disposed thereon;
         (A) the first flange adhesive layer on the first surface of the flange continuously surrounding the stoma-receiving aperture;
      (ii) the second surface of the flange including a second flange adhesive layer disposed thereon;
         (A) the second flange adhesive layer on the second surface of the flange continuously surrounding the stoma-recieving aperture; and
   (b) a tubular wail extending from the first surface of the flange; the tubular wall defining a wall stoma-receiving aperture in communication with the flange stoma-receiving aperture; the tubular wail having an inner, stoma-contacting surface and an opposite outer surface adapted to form a seal that inhibits material that is expelled through the stoma and into the pouch from passing between the stoma and the tubular wall to prevent material from leaking from the pouch and irritating the skin;
      (i) the inner, stoma-contacting surface including a stoma-contacting adhesive layer forming a continuous adhesive ring on the inner stoma-contacting surface of the tubular wall;
      (ii) the tubular wall having a length of at least 0.5 inch; and
      (iii) the first flange adhesive layer on the first surface of the flange continuously surrounds the outer surface of the tubular wall.

2. An adapter arrangement according to claim 1 wherein:
   (a) the flange stoma-receiving aperture and the wall stoma-receiving aperture are co-axial.

3. An adapter arrangement according to claim 1 wherein:
   (a) the tubular wall has a length that is twice that of a rim width of the flange.

4. An adapter arrangement according to claim 1 wherein:
   (a) the tubular wall extends from the flange at an angle of declination between 2 and 15 degrees.

5. An adapter arrangement according to claim 1 wherein:
   (a) the tubular wall extends from the flange at an angle of declination of 8 degrees.

6. An adapter arrangement according to claim 4 wherein:
   (a) the flange and tubular wall comprise a soft rubber.

7. An adapter arrangement according to claim 6 wherein:
   (a) the flange stoma-receiving aperture is circular and has a diameter of 0.5–2.5 inches.

8. A human waste collection system for use with a body part having a stoma projecting from a human body and surrounded by a portion of exterior skin; the collection system comprising:
   (a) an adapter arrangement including:
      (i) a flange having first and second opposite surfaces and defining a stoma-receiving aperture; the first surface of the flange including a first flange adhesive layer disposed thereon; the second surface of the flange including a second flange adhesive layer disposed thereon;
         (A) the first flange adhesive layer on the first surface of the flange continuously surrounding the stoma-receiver aperture;
         (B) the second flange adhesive layer on the second surface of the flange continuously surrounding the stoma-receiving aperture;
      (ii) a tubular wall extending from the first surface of the flange; the tubular wall defining wall stoma-receiving aperture in communication with the flange stoma-receiving aperture; the tubular wail having an inner, stoma-contacting surface and an opposite outer surface; the inner, stoma-contacting surface including a stoma-contacting adhesive layer, said stoma-contacting adhesive layer thereby forming a seal that inhibits material that is expelled through the stoma and into the pouch from passing between the stoma and the tubular wall to prevent material from leaking from the pouch and irritating the skin; the tubular wall having a length of at least 0.5 inch;
         (A) the first flange adhesive layer on the first surface of the flange continuously surrounds the outer surface of the tubular wall;
   (b) a waste collection pouch including:
      (i) a pouch wall defining: an interior waste collecting volume; and a mouth providing access to the volume;

(ii) a lip on the pouch wall circumscribing the mouth; and
(iii) an adhesive collar circumscribing the lip;
(c) the adapter tubular wall being received within the mouth; and
(d) the first flange adhesive layer securing the first surface of the flange to the pouch lip.

9. A human waste collection system according to claim 8 wherein:
(a) the stoma-contacting adhesive layer on the inner stoma-contacting surface of the tubular wall removably securing the adapter arrangement to the body part having the stoma.

10. A human waste collection system according to claim 9 wherein:
(a) the second flange adhesive layer removably secures the adapter arrangement to the portion of exterior skin.

11. A human waste collection system according to claim 10 wherein:
(a) the adhesive collar removably secures the waste collection pouch to the portion of exterior skin.

12. A human waste collection system according to claim 11 wherein:
(a) the flange stoma-receiving aperture and the wall stoma receiving aperture are co-axial;
(b) the tubular wall has a length that is at least twice that of a rim width of the flange;
(c) the tubular wall extends from the flange at an angle of declination between 2 and 15 degrees;
(d) the flange and tubular wall comprise a soft rubber; and
(e) the flange stoma-receiving aperture is circular and has a diameter of 0.5–2.5 inches.

13. A human waste collection system according to claim 8 wherein:
(a) the pouch wall defines at least one open end spaced from the mouth; and
(b) the waste collection pouch further includes a zipper closure to permit selective opening and closing of the at least one open end.

14. A human waste collection system according to claim 13 wherein:
(a) the pouch wall defines a second open end spaced from the mouth; and
(b) the waste collection pouch further includes a second zipper closure to permit selective opening and closing of the second open end.

15. An adapter arrangement for use with a waste collection construction; the adapter arrangement comprising:
(a) a flange having first and second opposite surfaces and defining a stoma-receiving aperture;
  (i) the first surface of the flange including a first flange adhesive layer disposed thereon;
    (A) the first flange adhesive liver on the first surface of the flange continuously surrounding the stoma-recieving aperture;
  (ii) the second surface of the flange including a second flange adhesive layer disposed thereon;
    (A) the second flange adhesive layer on the second surface of the flange continuously surrounding the stoma-receiving aperture; and
(b) a tubular wall extending from the first surface of the flange; the tubular wall defining a wall stoma-receiving aperture in communication with the flange stoma-receiving aperture; the tubular wall having an inner, stoma-contacting surface and an opposite outer surface;
  (i) the inner, stoma-contacting surface including a stoma-contacting adhesive layer forming a continuous adhesive ring on the inner stoma-contacting surface of the tubular wall adapted to form a seal that inhibits material that is expelled through the stoma and into the pouch from passing between the stoma and the tubular wall to prevent material from leaking from the pouch and irritating the skin;
  (ii) the flange stoma-receiving aperture and the wall stoma-receiving aperture being co-axial;
  (iii) the tubular wall having a length that is at least twice that of a rim width of the flange; and
  (iv) the first flange adhesive layer on the first surface of the flange continuously surrounds the outer surface of the tubular wall.

16. A human waste collection system for use with a body part having a stoma projecting from a human body and surrounded by a portion of exterior skin; the collection system comprising:
(a) an adapter arrangement including:
  (i) a flange having first and second opposite surfaces and defining a stoma-receiving aperture; the first surface of the flange including a first flange adhesive layer disposed thereon; the second surface of the flange including a second flange adhesive layer disposed thereon;
  (ii) a tubular wall extending from the first surface of the flange; the tubular wall defining a wall stoma-receiving aperture in communication with the flange stoma-receiving aperture; the tubular wall having an inner, stoma-contacting surface and an opposite outer surface; the inner, stoma-contacting surface including a stoma-contacting adhesive layer;
(b) a waste collection pouch including:
  (i) a pouch wall defining: an interior waste collecting volume; and a mouth providing access to the volume;
  (ii) a lip on the pouch wall circumscribing the mouth; and
  (iii) an adhesive collar circumscribing the lip;
(c) the adapter tubular wall being received within the mouth;
(d) the first flange adhesive layer seeming the first surface of the flange to the pouch lip;
(e) the stoma-contacting adhesive layer on the inner stoma-contacting surface of the tubular wall removably securing the adapter arrangement to the body part having the stoma, thereby forming a seal that inhibits material that is expelled through the stoma and into the pouch from passing between the stoma and the tubular wall to prevent material from leaking from the pouch and irritating the skin;
(f) the second flange adhesive layer removably securing the adapter arrangement to the portion of exterior skin;
(g) the adhesive collar removably securing the waste collection pouch to the portion of exterior skin;
(h) the flange stoma-receiving aperture and the wall stoma receiving aperture being co-axial;
(i) the tubular wall having a length that is at least twice that of a rim width of the flange;
(j) the tubular wall extending from the flange at an angle of declination between 2 and 15 degrees;
(k) the flange and tubular wall comprising a soft rubber; and
(l) the flange stoma-receiving aperture being circular and having a diameter of 0.5–2.5 inches.

17. A human waste collection system for use with a body part having a stoma projecting from a human body and surrounded by a portion of exterior skin; the collection system comprising:
(a) an adapter arrangement including:
  (i) a flange having first and second opposite surfaces and defining a stoma-receiving aperture; the first surface of the flange including a first flange adhesive layer disposed thereon; the second surface of the flange including a second flange adhesive layer disposed thereon;
  (ii) a tubular wall extending from the first surface of the flange; the tubular wall defining a wall stoma-receiving aperture in communication with the flange stoma-receiving aperture; the tubular wall having an inner, stoma-contacting surface and an opposite outer surface; the inner, stoma-contacting surface including a stoma-contacting adhesive layer thereby forming a seal that inhibits material that is expelled through the stoma and into the pouch from passing between the stoma and the tubular wall to prevent material from leaking from the pouch and irritating the skin;
  (iii) the tubular wall having a length that is at least twice that of a rim width of the flange;
(b) a waste collection pouch including:
  (i) a pouch wall defining; an interior waste collecting volume; and a mouth providing access to the volume;
  (ii) a lip on the pouch wall circumscribing the mouth; and
  (iii) an adhesive collar circumscribing the lip;
(c) the adapter tubular wall being received within the mouth; and
(d) the first flange adhesive layer securing the first surface of the flange to the pouch lip.

18. A human waste collection system for use with a body part having a stoma projecting from a human body and surrounded by a portion of exterior skin; the collection system comprising:
(a) an adapter arrangement including:
  (i) a flange having first and second opposite surfaces and defining a stoma-receiving aperture; the second surface of the flange including a flange adhesive layer disposed thereon;
    (A) the flange adhesive layer on the second surface of the flange continuously surrounding the stoma-receiving aperture;
  (ii) a tubular wall extending from the first surface of the flange; the tubular wall defining a wall stoma-receiving aperture in communication with the flange stoma-receiving aperture; the tubular wall having an inner, stoma-contacting surface and an opposite outer surface; the inner, stoma-contacting surface including a stoma-contacting adhesive layer layer forming a continuous adhesive ring on the inner stoma-contacting surface of the tubular wall thereby forming a seal that inhibits material that is expelled through the stoma and into the pouch from passing between the stoma and the tubular wall to prevent material from leaking from the pouch and irritating the skin;
    (A) the tubular wall having a length of at least 0.5 inch;
(b) a waste collection pouch including:
  (i) a pouch wall defining an interior waste collecting volume; and a mouth providing access to the volume;
  (ii) a lip on the pouch wall circumscribing the mouth; and
  (iii) an adhesive collar circumscribing the lip;
(c) the adapter arrangement being an integral part of the waste collection pouch;
  (i) the tubular wall of the adapter arrangement defining the pouch mouth; and
  (ii) the flange being an extension of the pouch lip.

19. A human waste collection system according to claim 18 wherein:
(a) the adhesive collar removably secures the waste collection pouch to the portion of exterior skin.

20. A human waste collection system according to claim 18 wherein:
(a) the pouch wall defines at least one open end spaced from the mouth; and
(b) the waste collection pouch further includes a zipper closure to permit selective opening and closing of the at least one open end.

* * * * *

UNITED STATES PATENT AND TRADEMARK OFFICE
CERTIFICATE OF CORRECTION

PATENT NO.       : 7,192,420 B2
APPLICATION NO.  : 10/637460
DATED            : March 20, 2007
INVENTOR(S)      : Whiteford It is certified that error appears in the above-identified patent and that said Letters Patent is hereby corrected as shown below:

Title page, (54) Title: "MULTIPLE ADHESIVES FOR RELIABLE SEALING" should read --MULTIPLE ADHESIVES/PASTE ARRANGEMENTS FOR RELIABLE SEALING--

Col. 1, lines 1-2: "MULTIPLE ADHESIVES FOR RELIABLE SEALING" should read --MULTIPLE ADHESIVES/PASTE ARRANGEMENTS FOR RELIABLE SEALING--

Col. 5, line 61, claim 1: "tubular wail extending" should read --tubular wall extending--

Col. 5, line 64, claim 1: "tubular wail having" should read --tubular wall having--

Col. 5, line 65, claim 1: "outer surface" should read --outer surface;--

Col. 5, lines 66-67 to Col. 6, lines 1-3, claim 1: "adapted to form" to "irritating the skin;" should be moved to the end of claim 1 (b)(i) after the words "tubular wall"

Col. 6, line 19, claim 4: "claim 1 wherein:" should read --claim 3 wherein:--

Col. 6, line 22, claim 5: "claim 1 wherein:" should read --claim 3 wherein:--

Col. 6, line 49, claim 8: "wall defining wall" should read --wall defining a wall--

Col. 6, line 51, claim 8: "tubular wail having" should read --tubular wall having--

UNITED STATES PATENT AND TRADEMARK OFFICE
CERTIFICATE OF CORRECTION

PATENT NO. : 7,192,420 B2
APPLICATION NO. : 10/637460
DATED : March 20, 2007
INVENTOR(S) : Whiteford It is certified that error appears in the above-identified patent and that said Letters Patent is hereby corrected as shown below:

Col. 7, line 55, claim 15: "recieving aperture;" should read --receiving aperture;--

Col. 8, line 43, claim 16: "layer seeming the" should read --layer securing the--

Signed and Sealed this

Eighth Day of January, 2008

JON W. DUDAS
*Director of the United States Patent and Trademark Office*